(12) United States Patent
Poynter et al.

(10) Patent No.: US 6,332,876 B1
(45) Date of Patent: Dec. 25, 2001

(54) COMPRESSIBLE SYRINGE

(76) Inventors: Richard Q. Poynter, 711 Pinehurst Way, Palm Beach Gardens, FL (US) 33419; Albert D. Bailey, 1133 The Pointe Dr., West Palm Beach, FL (US) 33409

( * ) Notice: Subject to any disclaimer, the term of this patent is extended or adjusted under 35 U.S.C. 154(b) by 292 days.

(21) Appl. No.: 08/925,053

(22) Filed: Sep. 8, 1997

(51) Int. Cl.$^7$ .................................................. A61M 5/178
(52) U.S. Cl. .......................................................... 604/212
(58) Field of Search .................................... 604/181, 185, 604/187, 200, 212–217; 222/541.5, 541.6, 541.9, 543, 212, 215, 107; 215/306; 220/375, 379, 744

(56) References Cited

U.S. PATENT DOCUMENTS 3,473,524 * 10/1969 Drewe ........................................ 128/2
4,262,669 * 4/1981 Sneider ................................. 128/232
5,242,422 * 9/1993 Schneberger et al. ............... 604/216

* cited by examiner

*Primary Examiner*—Sharon Kennedy

(57) ABSTRACT

A compressible syringe including a bellows, the rearward frusto-conical bellows walls are thicker than the forward frusto-conical bellows walls, the walls converge in an apex with the rearward frusto-conical wall at a first included angle with respect to a plane perpendicular to the longitudinal axis of the syringe and intersecting the apex and with the forward frusto-conical wall being at a second included angle with respect to the plane and with the first included angle being greater than the second included angle, the bellows rings increase in diameter successively from the rearward to the forward portion of the syringe and a fracture closure seal formed integrally with the syringe nozzle is provided and is connected to the syringe body by an elongate pliable tether.

6 Claims, 3 Drawing Sheets

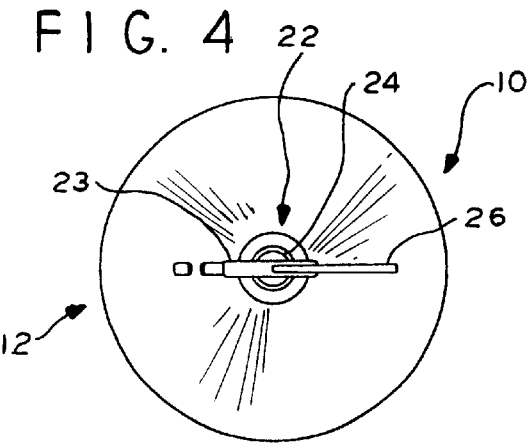
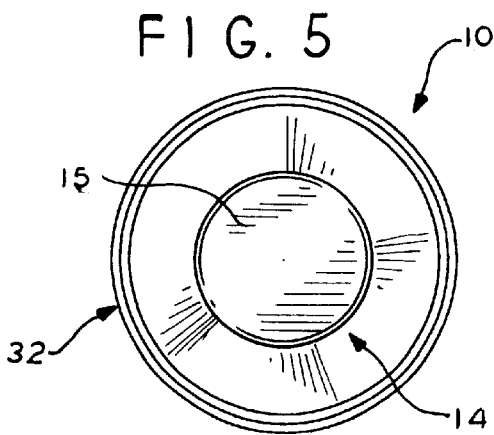
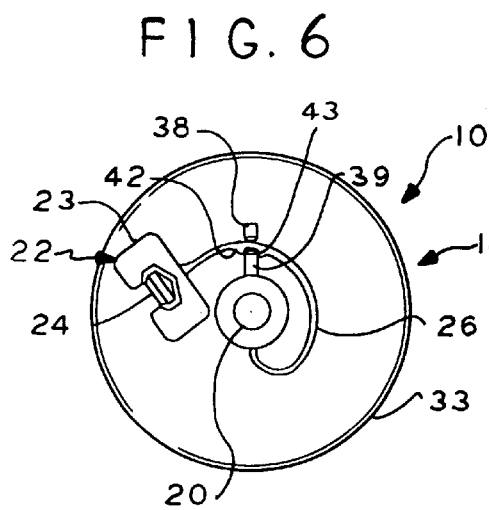
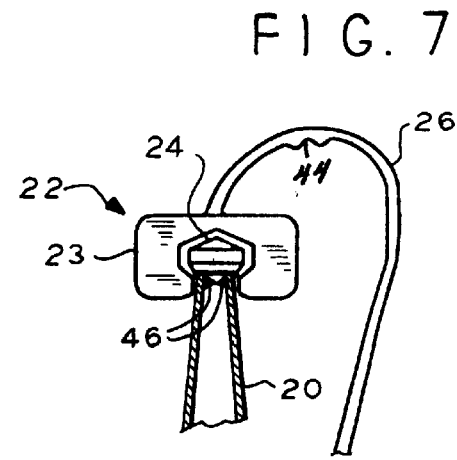
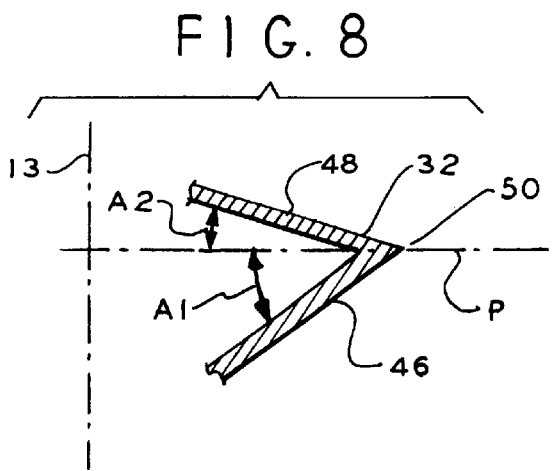

COMPRESSIBLE SYRINGE

FIELD OF THE INVENTION

This invention relates generally to a compressible syringe and more particularly relates to an improved pre-filled or liquid-filled compressible syringe.

BACKGROUND OF THE INVENTION

Compressible syringes, particularly molded compressible syringes, are generally known in the medical device art. Typical uses of such syringes include body irrigation such as bladder and wound irrigation and the dispensing or injection of liquids such as sterile water, saline solutions, liquid pharmaceuticals and other liquids, or semi-viscous materials capable of being dispensed from a compressible syringe, into, for example, a surgical wound or cavity.

A collapsible ampule is disclosed in U.S. Pat. No. 3,340,869 to Bane, patented Sep. 12, 1967, such ampule includes a bellows end section wherein the diameter of the bellows end section is larger than the diameters of the remaining bellows section and wherein the wall thickness of the rear wall of the bellows end section is less than the thickness of the forward wall of the bellows end section wherein upon axial compression of the bellows the bellows end section collapses into an inverted position with the rear wall lying close against the inner surface of the forward wall and having an inherent over-center bias which provides yielding resistance to initial displacement thereof out of the inverted fully collapsed position in the direction to expand the bellows section of which it forms a part. A one-piece disposable liquid-filled syringe is disclosed in U.S. Pat. No. 4,411,656 to Cornett, patented Oct. 25, 1983. The syringe disclosed in this patent includes a cap which an be removably placed over the tip of the syringe between uses to maintain the sterility of the contents of the syringe.

A one-piece molded syringe with tethered cap is disclosed in U.S. Pat. No. 2,242,422 to Schneberger et al., patented Sep. 7, 1993. The compressible syringe disclosed in this patent includes a fracturable closure seal formed integrally with the tip of a nozzle and which seal includes a closure cap which can be replaced over the nozzle tip after being removed to maintain the sterility of the syringe contents. The closure seal is connected to the syringe body by a tether and projections are provided on the syringe for engaging a correspondingly shaped cavity provided in the closure seal whereby the closure seal may be removably fastened to the syringe body during disuse.

SUMMARY OF THE INVENTION

A syringe having a hollow body including a bellows and a nozzle through which liquid contained in the bellows is ejected upon compression of the bellows, the bellows including at least one ring or bellows section including a rearward frusto-conical wall and a forward frusto-conical wall and which frusto-conical walls converge in an apex with the rearward wall being at a first included angle with respect to a plane perpendicular to the longitudinal axis of the syringe and intersecting the apex and with the forward frusto-conical wall being at a second included angle with respect to the plane and the first included angle may be greater than the second included angle. The thickness of the rearward frusto-conical wall may be greater than the thickness of the forward frusto-conical wall.

Further the bellows may include a plurality of rings which increase in diameter successively from a closed rear wall toward a forward nozzle.

Still further, the syringe may include a fracture closure seal formed integrally with the syringe nozzle and the closure seal may be connected to the hollow body of the syringe by an elongate pliable tether to prevent separation of the seal from the body.

DESCRIPTION OF THE DRAWINGS

FIG. 4 is a top view of the compressible syringe shown in FIG. 1;

FIG. 5 is a bottom view of the compressible syringe shown in FIG. 1;

FIG. 6 is a top view of the compressible syringe showing the fracturable closure seal removed from the nozzle and fastened to the syringe body by an elongate pliable tether;

FIG. 7 is an enlarged partial view showing the fracturable closure seal nozzle and tether of the present invention;

FIG. 8 is a diagrammatical illustration of a representative bellows ring having rearward and forward frusto-conical walls provided with different included angles with respect to a plane perpendicular to the longitudinal axis of the syringe and passing through the apex at which the walls converge;

DESCRIPTION OF THE PREFERRED EMBODIMENT

Figure 1:
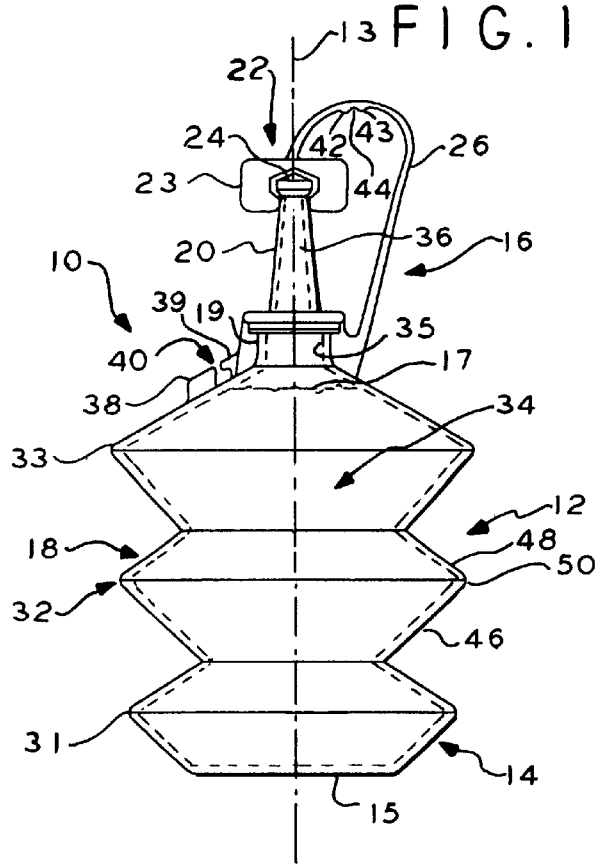
FIG. 1 is a front elevational view of a compressible syringe embodying the present invention.

Referring now to the drawings and in particular to FIGS. 1–5, there is shown a compressible syringe embodying the present invention and indicated by general numerical designation 10. Compressible syringe 10 includes a hollow body indicated by general numerical designation 12 and which hollow body includes a rearward portion indicated by general numerical designation 14, a forward portion indicated by general numerical designation 16, and an intermediate bellows or bellows portion indicated by general numerical designation 18.

The rearward portion 14 includes a closed rear wall 15. The rearward portion of the bellows 18 adjoins the closed rear wall 15, and the forward syringe portion 16 adjoins forward portion of the bellows 18 opposite the rear wall 15. The forward portion 16 of the compressible syringe includes a neck 19, a nozzle 20, a fracturable closure seal indicated by general numerical designation 22 and including a tab 23 and a sealing member 24, and an elongate pliable tether connecting the fracturable closure seal 22 to the hollow body 12. The tab 23 is generally planar and extends generally transversely with respect to the sealing member 24 as may be noted particularly in FIG. 4.

Figure 2:
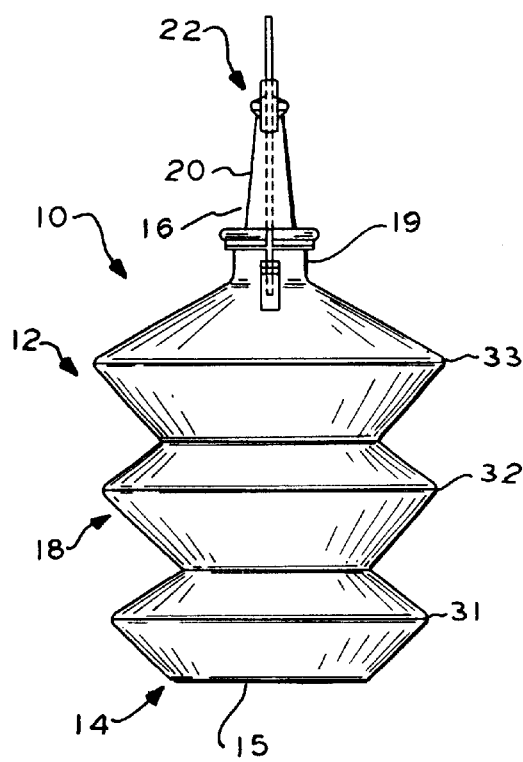
FIG. 2 is a left side view of the compressible syringe shown in FIG. 1.
Figure 3:
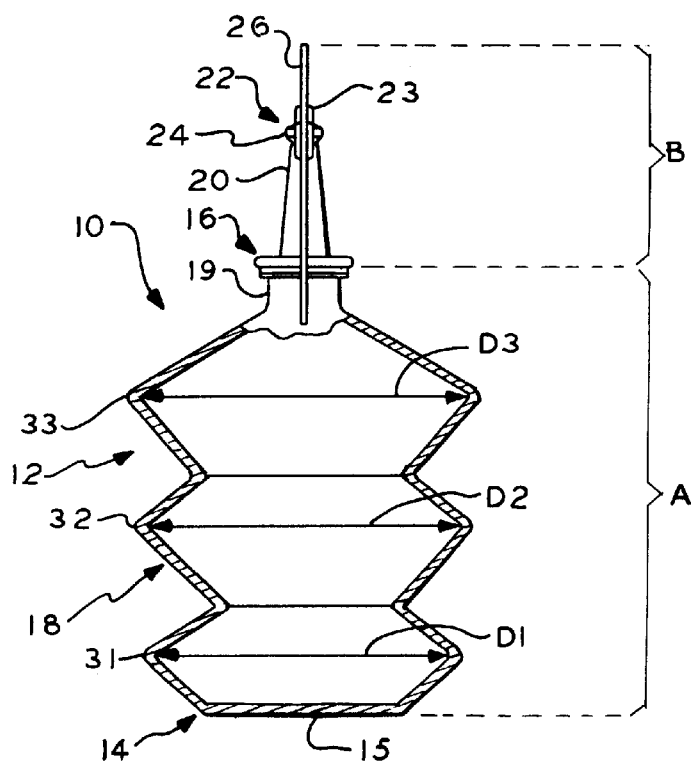
FIG. 3 is a right side view of the compressible syringe shown in FIG. 1.

Referring further to FIGS. 1, 2 and 3, the bellows 18, in the preferred embodiment, includes three bellows sections or bellows rings 31, 32 and 33. As indicated by the dashed lines in FIG. 1, the bellows rings 31, 32 and 33 are defined by walls providing the bellows 18 with a hollow interior indicated by general numerical designation 34, the neck 19 is provided with a passageway 35 and the nozzle 20 is provided with a passageway 36; the hollow bellows interior 34, the neck passageway 35, and the nozzle passageway 36 are in liquid flow communication.

From FIG. 3, it will be understood that the bellows ring 31 has a diameter D1, the bellows ring 32 has a diameter D2, and the bellows ring 33 has a diameter D3. From FIG. 3, it will be further understood that the diameters, i.e. the length of the diameters, of these bellows rings increase successively in length from the closed rear wall 15 toward the nozzle 20.

As shown particularly in FIGS. 1 and 6, the syringe body 18 may be provided with a pair of outwardly extending tabs or members 38 and 39 providing an indentation or notch 40 and the tether 26 may be provided with outwardly extending tabs 42 and 43 providing an inwardly extending indentation or notch 44. As indicated in FIG. 6, upon the fracture closure seal 22, particularly the sealing member 24, being fractured and broken away from the outer end or tip of the nozzle 20 to permit the dispensing of liquid upon the bellows 18 being compressed, the pairs of tabs 38 and 39 and 42 and 43 may be snap-fitted together with the notch 40 (FIG. 1) receiving a portion of the tether 26 and with the notch 44 (FIG. 1) receiving the tab 39 as shown in FIG. 6 to fasten the tether 26 to the syringe body 18 thereby fastening the closure seal 22 to the syringe body. The tether 26 prevents the fracturable closure seal 22 from being physically separated from, or disassociated from, the syringe body 18 which, for example, prevents the fracturable closure seal 22 from falling into a surgical wound or cavity and inadvertently remaining therein after the surgical cavity or wound is closed.

The compressible syringe 10 of the present invention may be a one-piece molded syringe molded, liquid-filled, and sealed by the blow fill seal technique practiced by blow fill seal machines available from Automatic Liquid Packaging Inc. of Woodstock, Ill. and from Vital Pharma, Inc. of Riviera Beach, Fla. In such blow fill seal molding, it will be understood that the compressible syringe 10 is made from a continuous extruded plastic parison and that the bellows 18 is made by blow molding, the neck 19 and nozzle 20 made by vacuum forming, and the closure seal 22, tether 26, tabs 39 and 40 and 42 and 43 made by compression molding; the neck 19 and nozzle 20 may be made by a combination of blow molding and vacuum forming. It will be understood from FIG. 3 that in such blow fill seal molding the lower portion A is first molded, the bellows are filled with liquid up to about the fill line 17 shown in FIG. 1 and the balance of the upper portion B of the syringe is then molded and sealed. From FIG. 1 it will be noted from the dashed lines that the diameter of the neck 19 is larger than the average diameter of the nozzle which is tapered. This permits the bellows to be filled with liquid faster than filling through the nozzle would permit.

From FIG. 7, it will be understood that in such blow fill seal molding the sealing member 24 is formed integrally with the tip or outer end of the nozzle 20 and is connected thereto by a thin annular portion or fracture ring indicated by the arrows 45 which fracture ring is thinner than the wall thickness of the nozzle 20 to facilitate fracture and breaking away of the closure seal member from the outer end of the nozzle. It will be understood that the tab 23 facilitates the application of torque to the sealing member 24 to fracture the ring 45 and facilitate the breaking of the sealing member 24 away from the tip or outer end of the nozzle 20.

Referring now to FIG. 8 and to an outer cross-sectional portion of representative bellows ring 32, it will be understood that the frusto-conical walls defining each bellows section or bellows ring may be disposed at different included angles with respect to the syringe longitudinal axis 13 shown completely in FIG. 1 and partially in FIG. 8, and described above. More specifically, and referring to FIGS. 1 and 8 and in particular FIG. 8, the representative bellows ring 32 includes a rearward frusto-conical wall 46 disposed toward said closed rear wall 15 (FIG. 1) and a forward frusto-conical wall 48 disposed toward the nozzle 20 (FIG. 1). The frusto-conical walls 46 and 48 converge at an apex 50. As may be noted particularly from FIG. 8, the rearward frusto-conical wall 46 is at an included angle A1 with respect to a plane P perpendicular to the longitudinal syringe axis 13 and extending through the apex 50 and the forward frusto-conical wall 48 is at an included angle A2 with respect to the plane P. It will be further understood from FIG. 8, that the angle A1 is greater than the angle A2 and in the preferred embodiment the angle A1 is about 45° and the angle A2 is from about 30° to about 35°.

Figure 9:
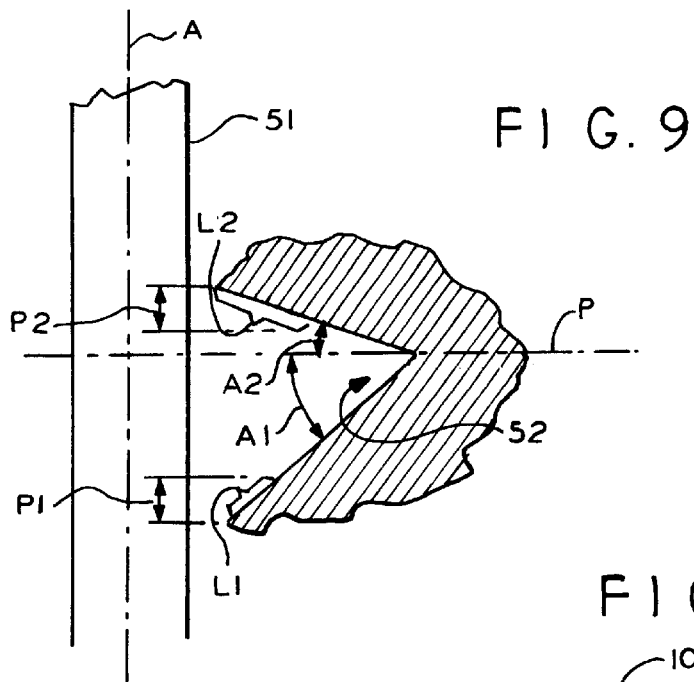
FIG. 9 is a diagrammatical illustration teaching how the frusto-conical walls defining a representative bellows of the present invention may be provided with different wall thicknesses.

It will be further understood from FIG. 9 that such difference in included angles A1 and A2 between the rearward frusto-conical walls and forward frusto-conical walls defining the bellows rings of the present invention provides the rearward frusto-conical walls with a greater thickness than the thickness of the forward frusto-conical walls upon portions of an extruded plastic parison 51 being blow molded into a mold cavity such as the partially shown mold cavity indicated by general numerical designation 52 in FIG. 9. It will be understood from FIG. 9 that, by way of example, axial lengths P1 and P2 of the extruded plastic parison 51 are of equal length and are blow molded into the cavity 52 to respectively form portions of the rearward frusto-conical wall 46 and the forward frusto-conical wall 48 shown in FIG. 8. More particularly, it will be understood that the parison axial length P1 is blow molded into the cavity 52 and stretched to form a portion or length L1 of the rearward frusto-conical wall 46 (FIG. 8) and that the parison axial length P2 is blow molded into the cavity 52 and stretched to form a portion or length L2 of the forward frusto-conical wall 48 (FIG. 8). As shown in FIG. 9, the length L1 is shorter than the length L2 which means that the parison length P2 is stretched less than the parison length P1 whereby the thickness of the length L1 will be greater than the thickness of the length L2 with the result being that upon the rearward and forward frusto-conical walls being fully blow molded by respective portions of the parison 51 the thickness of the rearward frusto-conical wall 46 (FIG. 8) will be thicker than the thickness of the forward frusto-conical wall 48 (FIG. 8).

Figure 10:
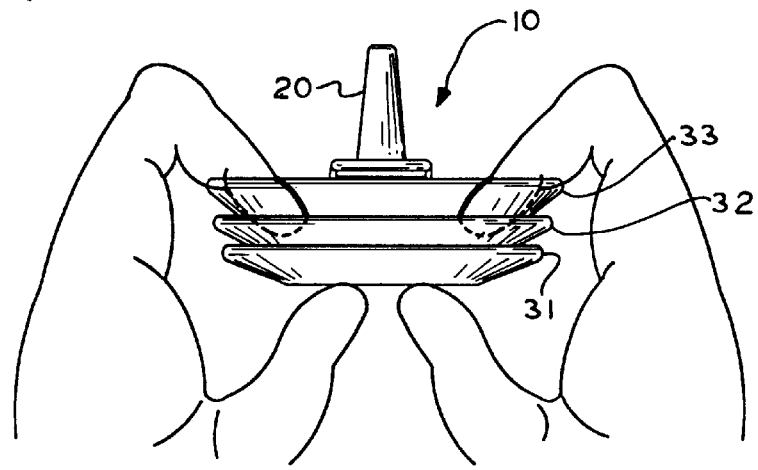
FIG. 10 is a diagrammatical view illustrating the compression of the syringe bellows by inversion of the rings comprising the bellows.

It has been discovered that the difference in lengths of the diameters D1, D2 and D3 of the respective bellows rings 31, 32 and 33 (FIG. 3), the difference in included angles A1 and A2 of the rearward and forward frusto-conical walls of the bellows ring (FIG. 8) and the difference in thickness between the rearward and forward frusto-conical walls defining the bellows rings 31, 32 and 33 (FIG. 8) causes the bellows rings 31, 32 and 33 to collapse by inversion rather than compression as do the bellows rings shown in U.S. Pat. Nos. 4,411,656 and 5,242,422, incorporated herein by reference above, upon collapsing force being applied to the bellows rings 31, 32 and 33, FIG. 10, by the fingers and thumbs of a person as shown in FIG. 10 to collapse the bellows rings and eject or dispense liquid contained in the syringe through the nozzle 20. From FIG. 10, it will be understood that the bellows rings 31, 32 and 33 of the present invention upon collapsing by inversion are stacked together in the same manner as pie tins or pans are stacked. This collapse of the bellows rings by inversion causes the bellows rings to collapse into a shorter axial distance or length than do the above-noted bellows rings which collapse by compression, whereby the hold-over portion, or residual liquid contained in the syringe after bellows compression, is less than would be contained in the syringe after bellows collapse were the rings to collapse by compression. This means that more of the liquid contained in the syringe is ejected or dispensed upon the bellows rings collapsing by inversion.

Figure 11:
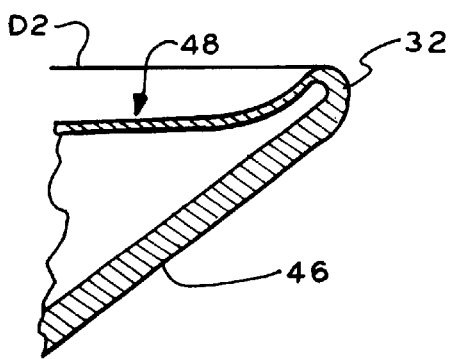
FIG. 11 is a partial cross-sectional view of a representative bellows ring illustrating collapse by inversion.

A further illustration of the collapse of a single bellows ring by inversion according to the present invention is illustrated in FIG. 11 with respect to a partial cross-sectional showing of representative bellows 32. Upon collapsing force being applied to the bellows as illustrated in FIG. 10 and described above, the forward frusto-conical wall 48 of the bellows ring 32 will collapse by inversion toward the rearward frusto-conical wall 46 and will pass below the bellows diameter D2 as shown in FIG. 11. This inversion collapse, as noted above, is due to the forward frusto-conical wall 48 being thinner than the rearward frusto-conical wall 46 as described above with regard to FIG. 9 and due to the forward frusto-conical wall 48 being at a lesser included angle A2 with respect to the plane P shown in FIG. 9 than the rearward frusto-conical wall 46 as described above.

It will be understood by those skilled in the art that many variations and modifications may be made in the present invention without departing from the spirit and the scope thereof.

What is claimed is:

1. A one piece molded syringe, comprising:
a hollow body at least partially filled with liquid, said hollow body having a longitudinal axis, a closed rear wall, a bellows adjoining said closed rear wall, and a forward portion adjoining said bellows opposite said rear wall and including a nozzle having an outer end;
a fracturable closure seal formed integrally with said outer end of said nozzle for closing said nozzle until initial use of said syringe;
an elongate pliable tether connected to said seal and said hollow body and connecting said seal to said hollow body to prevent separation of said seal from said hollow body;
first fastening means provided on said hollow body and second fastening means provided on said tether and said fastening means for being engaged to fasten said tether to said hollow body upon said seal being broken away from said outer end of said nozzle, said first fastening means comprising a pair of tabs extending outwardly from said body and providing a first indentation therebetween and said second fastening means comprising a portion of said tether providing a second indentation and wherein said indentations are engageable to fasten said tether to said body;
said bellows including a plurality of bellow rings each having a diameter and wherein the diameters of said bellows rings increase successively from said rear wall toward said nozzle;
each bellows ring including a rearward frusto-conical wall having a thickness and disposed toward said closed rear wall and a forward frusto-conical wall having a thickness and disposed toward said nozzle and wherein the thickness of said rearward frusto-conical wall is greater than the thickness of said forward frusto-conical wall, said walls converging at an apex and said rearward frusto-conical wall at a first included angle with respect to a plane perpendicular to said axis and extending through said apex and said forward frusto-conical wall at a second included angle with respect to said plane and said first included angle being greater than said second included angle;
said fracturable closure seal including a sealing member formed integrally with and extending transversely with respect to said sealing member and for having torque applied thereto to fracture and remove said sealing member from said outer end of said nozzle; and
wherein said first included angle is about 45° and wherein said second included angle is from about 30° to about 35°.

2. In a syringe having a hollow body including a closed rear wall, a bellows and a nozzle through which liquid contained in the syringe is ejected upon compression of the bellows, said syringe having a longitudinal axis and the bellows including at least one bellows ring including a rearward frusto-conical wall disposed toward said closed rear wall and a forward frusto-conical wall disposed toward said nozzle and wherein the frusto-conical walls converge at an apex,
wherein the improvement comprises:
said rearward frusto-conical wall at a first included angle with respect to a plane perpendicular to said axis and intersecting said apex and said forward frusto-conical wall at a second included angle with respect to said plane and wherein said first included angle is greater than said second included angle;
said nozzle having an outer end and said syringe further comprising a fracturable closure seal formed integrally with said outer end of said nozzle and for closing said nozzle until initial use of said syringe and an elongate pliable tether connected to said seal and said hollow body and connecting said seal to said body to prevent separation of said seal from said body;
said body provided with first fastening means, said tether provided with second fastening means and said fastening means being engageable to fasten said tether to said body upon said seal being broken away from said outer end of said nozzle; and
said first fastening means comprising a pair of tabs extending outwardly from said body and providing a first indentation therebetween and said second fastening means comprising a portion of said tether providing a second indentation and wherein said indentations are engageable to fasten said tether to said body.

3. In a syringe having a hollow body including a closed rear wall, a bellows and a nozzle through which liquid contained in the syringe is ejected upon compression of the bellows, said syringe having a longitudinal axis and the bellows including at least one bellows ring including a rearward frusto-conical wall having a thickness and disposed toward said closed rear wall and a forward frusto-conical wall having a thickness and disposed toward said nozzle and wherein the frusto-conical walls converge at an apex,
wherein the improvement comprises:
said thickness of said rearward frusto-conical wall being greater than the thickness of said forward frusto-conical wall, and
said rearward frusto-conical wall at a first included angle with respect to a plane perpendicular to said axis and intersecting said apex and said forward frusto-conical wall at a second included angle with respect to said plane and wherein said first included angle is greater than said second included angle;

said nozzle having an outer end and wherein said syringe further comprising a fracturable closure seal formed integrally with said outer end of said nozzle and for closing said nozzle until initial use of said syringe and an elongate pliable tether connected to said seal and said hollow body and connecting said seal to said body to prevent separation of said seal from said body;

said body provided with first fastening means, said tether provided with second fastening means and said fastening means being engageable to fasten said tether to said body upon said seal being broken away from said outer end of said nozzle; and said first fastening means comprising a pair of tabs extending outwardly from said body and providing a first indentation therebetween and said second fastening means comprising a portion of said tether providing a second indentation and wherein said indentations are engageable to fasten said tether to said body.

4. In a syringe including a bellows having a longitudinal axis, the bellows including a plurality of bellows rings and each bellows ring including a first frusto-conical wall and a second frusto-conical wall and wherein the frusto-conical walls converge at an apex, wherein the improvement comprises:
said first frusto-conical wall at a first included angle with respect to a plane perpendicular to said axis and intersecting said apex and said second frusto-conical wall at a second included angle with respect to said plane and wherein said first included angle is greater than said second included angle;

said syringe having a forward portion and a rearward portion, each of said bellows rings having a diameter and the diameters of said bellows rings increasing successively from said rearward portion to said forward portion of said syringe; and said first included angle being greater than said second included angle and said diameters of said bellows rings increasing successively from said rearward portion to said forward portion of said syringe causing said bellows rings to collapse by inversion upon collapsing force being applied to said bellows rings.

5. In a syringe having a hollow body including a closed rear wall, a bellows and a nozzle through which liquid contained in the syringe is ejected upon compression of the bellows, said syringe having a longitudinal axis and the bellows including a plurality of bellows rings and each bellows ring including a rearward frusto-conical wall disposed toward said closed rear wall and a forward frusto-conical wall disposed toward said nozzle and wherein the frusto-conical walls converge at an apex, wherein the improvement comprises:
said rearward frusto-conical wall at a first included angle with respect to a plane perpendicular to said axis and intersecting said apex and said forward frusto-conical wall at a second included angle with respect to said plane and wherein said first included angle is greater than said second included angle;

said syringe having a forward portion and a rearward portion, each of said bellows rings having a diameter and the diameters of said bellows rings increasing successively from said rearward portion to said forward portion of said syringe; and said first included angle being greater than said second included angle and said diameters of said bellows rings increasing successively from said rearward portion to said forward portion of said syringe causing said bellows rings to collapse by inversion upon collapsing force being applied to said bellows rings.

6. In a syringe having a hollow body including a closed rear wall, a bellows and a nozzle through which liquid contained in the syringe is ejected upon compression of the bellows, said syringe having a longitudinal axis and the bellows including a plurality of bellows rings and each bellows ring including a rearward frusto-conical wall having a thickness and disposed toward said closed rear wall and a forward frusto-conical wall having a thickness and disposed toward said nozzle and wherein the frusto-conical walls converge at an apex, wherein the improvement comprises:
said thickness of said rearward frusto-conical wall being greater than the thickness of said forward frusto-conical wall, and said rearward frusto-conical wall at a first included angle with respect to a plane perpendicular to said axis and intersecting said apex and said forward frusto-conical wall at a second included angle with respect to said plane and wherein said first included angle is greater than said second included angle;

said syringe having a forward portion and a rearward portion, each of said bellows rings having a diameter and the diameters of said bellows rings increasing successively from said rearward portion to said forward portion of said syringe; and said thickness of said rearward frusto-conical wall being greater than the thickness of said forward frusto-conical wall, said first included angle being greater than said second included angle and said diameters of said bellows rings increasing successively from said rearward portion to said forward portion of said syringe causing said bellows rings to collapse by inversion upon collapsing force being applied to said bellows rings.

* * * * *